United States Patent
Chiba et al.

(10) Patent No.: US 9,468,381 B2
(45) Date of Patent: Oct. 18, 2016

(54) DIAGNOSTIC SYSTEM

(75) Inventors: Toru Chiba, Tokyo (JP); Yoshimi Obara, Tokyo (JP); Makoto Hashizume, Fukuoka (JP); Takayuki Matsumoto, Fukuoka (JP); Kozo Konishi, Oita (JP); Morimasa Tomikawa, Fukuoka (JP); Masaharu Murata, Fukuoka (JP)

(73) Assignees: KYUSHU UNIVERSITY, NATIONAL UNIVERSITY CORPORATION, Fukuoka (JP); HOYA CORPORATION, Tokyo (JP)

( * ) Notice: Subject to any disclaimer, the term of this patent is extended or adjusted under 35 U.S.C. 154(b) by 74 days.

(21) Appl. No.: 13/877,979

(22) PCT Filed: Sep. 6, 2011

(86) PCT No.: PCT/JP2011/070216
§ 371 (c)(1),
(2), (4) Date: Apr. 5, 2013

(87) PCT Pub. No.: WO2012/046530
PCT Pub. Date: Apr. 12, 2012

(65) Prior Publication Data
US 2013/0197371 A1    Aug. 1, 2013

(30) Foreign Application Priority Data
Oct. 7, 2010   (JP) ................ 2010-227295

(51) Int. Cl.
*A61B 6/00* (2006.01)
*A61B 1/06* (2006.01)
(Continued)

(52) U.S. Cl.
CPC ........... *A61B 5/0084* (2013.01); *A61B 1/0638* (2013.01); *A61B 1/0646* (2013.01);
(Continued)

(58) Field of Classification Search
CPC ............ A61B 5/0075; A61B 5/14546; A61N 5/0601

USPC ....... 600/476, 477, 109, 160, 178, 179, 180, 600/181
See application file for complete search history.

(56) References Cited

U.S. PATENT DOCUMENTS 5,042,494 A * 8/1991 Alfano .................... 600/477
5,078,150 A * 1/1992 Hara et al. .............. 600/476
(Continued)

FOREIGN PATENT DOCUMENTS

| CN | 101188965 | 5/2008 |
| CN | 101461706 | 6/2009 |

(Continued)

OTHER PUBLICATIONS

Japan Office action in Japan Patent Application No. 2010-227295, dated Sep. 2, 2014 along with an english translation thereof.
(Continued)

*Primary Examiner* — Anhtuan T Nguyen
*Assistant Examiner* — William Chou
(74) *Attorney, Agent, or Firm* — Greenblum & Bernstein P.L.C.

(57) ABSTRACT

A diagnostic system comprises a spectral image shooting means that shoots a spectral image within a predetermined wavelength range in a body cavity and obtains spectral image data, an image processing means that obtains the spectral image data and calculates an indicator indicating an area having a high possibility of a diseased portion from the spectral image data, and a monitor on which the indicator is displayed, and wherein the image processing means calculates, as the indicator, a ratio between an accumulated value of intensity values of all spectral images in the predetermined wavelength range and an intensity value of spectral images in a particular wavelength band, for each coordinate in the spectral image.

8 Claims, 5 Drawing Sheets

(51) Int. Cl.
  *A61B 5/00* (2006.01)
  *G06T 7/00* (2006.01)

(52) U.S. Cl.
  CPC ........... *A61B5/0075* (2013.01); *A61B 5/4238* (2013.01); *A61B 5/4283* (2013.01); *G06T 7/0012* (2013.01); *G06T 2207/10024* (2013.01); *G06T 2207/10068* (2013.01); *G06T 2207/30092* (2013.01); *G06T 2207/30096* (2013.01)

(56) References Cited

U.S. PATENT DOCUMENTS

| | | | |
|---|---|---|---|
| 5,467,767 A * | 11/1995 | Alfano et al. | 600/476 |
| 6,465,968 B1 | 10/2002 | Sendai | |
| 7,123,756 B2 | 10/2006 | Hakamata et al. | |
| 7,236,621 B2 | 6/2007 | Kobayashi et al. | |
| 2002/0138008 A1 | 9/2002 | Tsujita et al. | |
| 2002/0168096 A1 | 11/2002 | Hakamata et al. | |
| 2003/0218137 A1 * | 11/2003 | Sendai | A61B 5/0071 250/461.1 |
| 2004/0064053 A1 * | 4/2004 | Chang et al. | 600/478 |
| 2004/0148141 A1 | 7/2004 | Tsujita et al. | |
| 2007/0219439 A1 * | 9/2007 | Vilser et al. | 600/323 |
| 2009/0118578 A1 | 5/2009 | Takasugi et al. | |
| 2009/0202119 A1 | 8/2009 | Hefti et al. | |
| 2009/0312644 A1 | 12/2009 | Kosugi et al. | |
| 2010/0119110 A1 * | 5/2010 | Kanda | 382/103 |
| 2012/0191365 A1 | 7/2012 | Chiba | |

FOREIGN PATENT DOCUMENTS

| | | |
|---|---|---|
| JP | 2001-070229 | 3/2001 |
| JP | 2001-128925 | 5/2001 |
| JP | 2001-258820 | 9/2001 |
| JP | 2003-528 | 1/2003 |
| JP | 2003-36436 | 2/2003 |
| JP | 2005-40181 | 2/2005 |
| JP | 2005-65976 | 3/2005 |
| JP | 2007-135989 | 6/2007 |
| JP | 2007-143647 | 6/2007 |
| JP | 2009-39280 | 2/2009 |
| JP | 2009-300131 | 12/2009 |

OTHER PUBLICATIONS

China Office Action in China Patent Application No. 201180048357.1, mail date is Jul. 3, 2015, together with an English language translation thereof.

Office Action issued in China Counterpart Patent Appl. No. 201180048357.1, dated Jan. 5, 2016, along with an English translation thereof.

* cited by examiner (a)

(b)

DIAGNOSTIC SYSTEM

TECHNICAL FIELD

The present invention relates a diagnostic system which generates an indicator indicating an area having a high possibility of a diseased portion in a living tissue.

BACKGROUND ART

Recently, an electronic endoscope having the function as a spectrometer has been proposed as described, for example, in Japanese Patent Provisional Publication No. 2007-135989A. By using such an endoscope, it is possible to obtain a spectral property (a light absorptivity distribution with respect to frequencies) of a living tissue, such as a mucous membrane of a digestive organ, e.g., a stomach or a rectum. It is known that a spectral property of a substance reflects information concerning the types or densities of components contained in the vicinity of a surface layer of a living tissue being an observation target, which is established in a field belonging to academic frameworks of the analytical chemistry. It is also known in this field that the spectral property of a substance consisting of a composite reflects information obtained by superimposing spectral properties of essential components constituting the composite.

There is a case where a substance having a chemical configuration, which is rarely contained in a living tissue of a healthy portion, is contained in a living tissue of a diseased portion. Therefore, the spectral property of a living tissue containing a diseased portion is different from the spectral property of a living tissue containing only a healthy portion. Since the spectral properties of healthy and diseased portions are different from each other as described above, it becomes possible to judge whether or not a living tissue contains a diseased portion by comparing the spectral properties of the healthy portion and the diseased portion.

SUMMARY OF THE INVENTION

As described above, by obtaining spectral information in a living body, it becomes possible to judge existence of a diseased portion in a living tissue from the spectral property. However, a method for making a judgment as to where a spectral property caused by a diseased portion exists in a living tissue and thereby identifying a position and an area of the diseased portion has not been proposed.

The present invention is made to solve the above described problem. That is, the object of the present invention is to provide a diagnostic system for generating an indicator useful for judging an area of a diseased portion in a living tissue.

To achieve the above described object, the diagnostic system according to the invention comprises: a spectral image shooting means that shoots a spectral image within a predetermined wavelength range in a body cavity and obtains spectral image data; an image processing means that obtains the spectral image data and calculates an indicator indicating an area having a high possibility of a diseased portion from the spectral mage data; and a monitor on which the indicator is displayed. The image processing means calculates, as the indicator, a ratio between an accumulated value of intensity values of all spectral images in the predetermined wavelength range and an intensity value of spectral images in a particular wavelength band, for each coordinate in the spectral image.

As described above, regarding the spectral property of a diseased portion in a living tissue, the intensity in the particular wavelength band differs from that of a healthy portion. However, it is difficult to keep the reflection angle of a biomaterial constant. Therefore, regarding the spectrum obtained from the spectral image data, the total light amount changes depending on the illumination angle of illumination light to the material. For this reason, according to the invention, an accumulated value of intensity values of image pixels of spectral images is obtained first, and the intensity values of the image pixels are normalized based on the accumulated value. A ratio between a spectral intensity of a target wavelength band of a particular image pixel and an accumulated intensity of intensity values of the particular image pixel is obtained, and fluctuation of the intensity values by the illumination angle of the illumination light and the material is corrected. The indicator obtained by this process indicates a ratio of the spectral property of the particular wavelength band with respect to the whole wavelength range. For example, an area having a larger ratio represents that the intensity component of the target wavelength range is large, i.e., the spectral property change is prominent relative to the other area. Furthermore, when the spectral property change specific to a diseased portion is known, the area is represented as an area to be noted as a diseased portion. When spectral information of a two dimensional area is available, it becomes possible to obtain disease information as a result of an area diagnosis by performing the above described process for each of the image pixels.

It is preferable that the image processing means may operate to display, on the monitor, an indicator graph which is a graphic representation of the indicator.

With this configuration, it becomes possible to easily judge which area has a high possibility of a diseased portion by referring to the indicator graph.

The image processing means may generate color image data by combining data of wavelength bands of a blue color, a green color and a red color of the spectral mage data; and the color image data and the indicator graph may be arranged side by side and may be displayed on the monitor.

With this configuration, it becomes possible to easily judge which area has a high possibility of a diseased portion by making a comparison between a color image of a living tissue shot by the spectral image shooting means and the indicator graph.

It is preferable that the particular wavelength band is a wavelength band whose maximum wavelength is smaller than an absorption wavelength band of hemoglobin of 550 nm to 590 nm. For example, the particular wavelength band is 480 nm to 520 nm.

As described above, according to the invention, it is possible to obtain an indicator useful for judging an existence area of a disease in a living tissue.

BRIEF DESCRIPTION OF THE DRAWINGS

FIG. 2(a) is a graph illustrating an example of a spectrum of a healthy portion of the gastric mucosa, and FIG. 2(b) is a graph illustrating an example of a diseased portion of the gastric mucosa.

EMBODIMENTS FOR CARRYING OUT THE INVENTION

In the following, an embodiment according to the invention is described with reference to the accompanying drawings.

Figure 1:
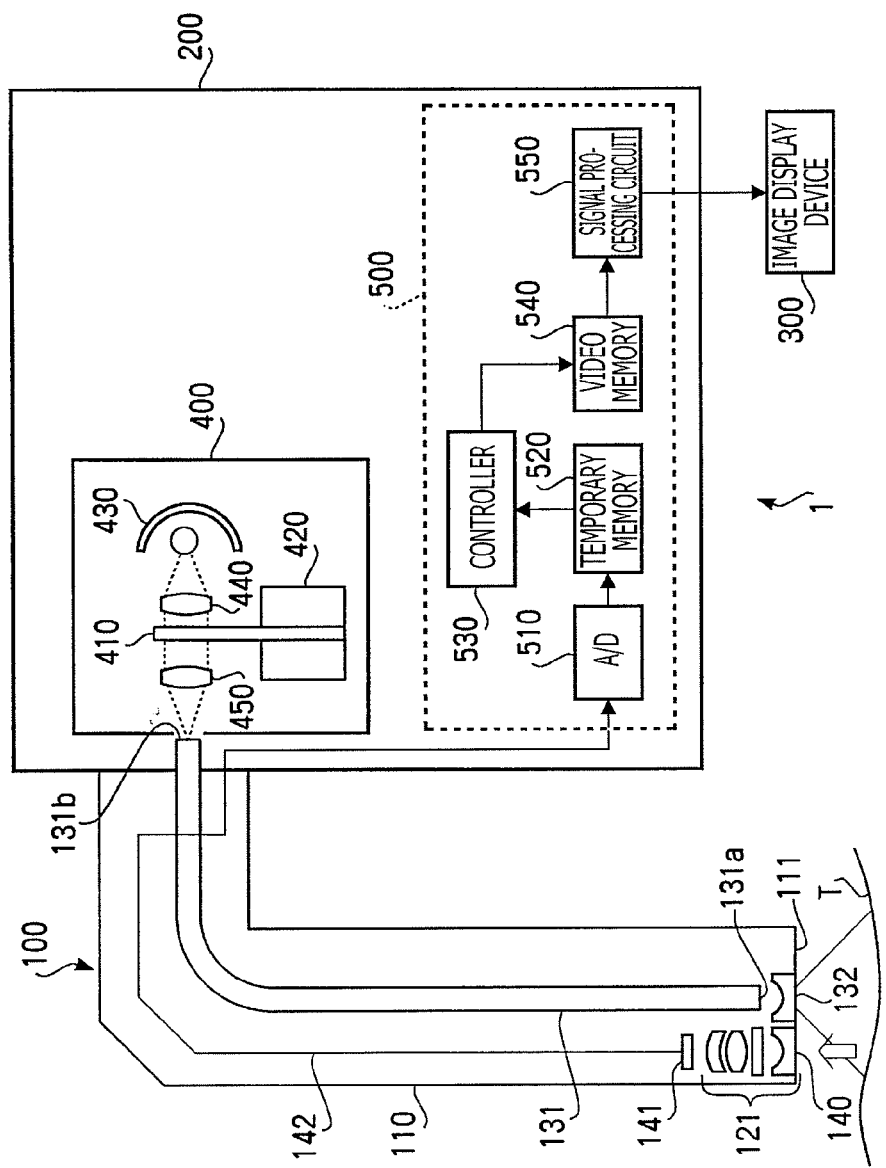
FIG. 1 is a block diagram illustrating a diagnostic system according to an embodiment of the invention.

FIG. 1 is a block diagram of a diagnostic system 1 according to the embodiment. The diagnostic system 1 according to the embodiment is configured to generate an indicator image to be referred to by a doctor for diagnosing a disease of a digestive organ, such as a stomach or a rectum. The diagnostic system 1 includes an electronic endoscope 100, a processor 200 for an electronic endoscope and an image display device 300. In the processor 200 for an electronic endoscope, a light source unit 400 and an image processing unit 500 are accommodated.

The electronic endoscope 100 includes an insertion tube 110 to be inserted into a body cavity, and an objective optical system 121 is provided at a tip portion (an insertion tube tip portion) 111 of the insertion tube 110. An image of a living tissue T around the insertion tube tip portion 111 is formed by the objective optical system 121 on a light-receiving surface of an image pick-up device 141 accommodated in the insertion tube tip portion 111.

The image pick-up device 141 periodically (e.g., at intervals of 1/30 seconds) outputs an image signal corresponding to the image formed on the light-receiving surface. The image signal outputted by the image pick-up device 141 is transmitted to the image processing unit 500 of the processor 200 for an electronic endoscope via a cable 142.

The image processing unit 500 includes an AD conversion circuit 510, a temporary memory 520, a controller 530, a video memory 540 and a signal processing circuit 550. The AD conversion circuit 510 executes the AD conversion for the image signal transmitted from the image pick-up device 141 of the electronic endoscope 100 via the cable 142 to output digital image data. The digital image data outputted from the AD conversion circuit 510 is transmitted to and stored in the temporary memory 520. The controller 530 processes a piece of or a plurality of pieces of image data stored in the temporary memory 520 to generate one piece of display image data, and transmits the display image data to the video memory 540. For example, the controller 530 produces the display image data generated from a piece of image data, the display image data in which a plurality of pieces of image data are arranged and displayed, or the display image data in which an image obtained by subjecting a plurality of pieces of image data to an image operation and a graph obtained as a result of the image operation are displayed, and stores them in the video memory 540. The signal processing circuit 550 converts the display image data stored in the video memory 540 into a video signal having a predetermined format (e.g., an NTSC format), and outputs the video signal. The video signal outputted from the signal processing circuit 550 is inputted to the image display device 300. As a result, an endoscopic image shot by the electronic endoscope 100 is displayed on the image display device 300.

A light guide 131 is provided in the electronic endoscope 100. A tip portion 131a of the light guide 131 is arranged close to the insertion tube tip portion 111, and a proximal end portion 131b of the light guide 131 is connected to the processor 200 for an electronic endoscope. The processor 200 for an electronic endoscope includes therein the light source unit 400 (described later) having a light source 430 generating a large amount of white light, e.g., a Xenon lamp. Light generated by the light source unit 400 is incident on the proximal end portion 131b of the light guide 131. The light which has entered into the proximal end portion 131b of the light guide 131 is guided to the tip portion 131a through the light guide 131, and is emitted from the tip portion 131a. In the vicinity of the tip portion 131a of the light guide 131 in the insertion tube tip portion 111 of the electronic endoscope 100, a lens 132 is provided. The light emitted from the tip portion 131a of the light guide 131 passes through the lens 132, and illuminates the living tissue T near the insertion tube tip portion 111.

As described above, the processor 200 for an electronic endoscope has both the function as a video processor which processes the image signal outputted from the image pick-up device 141 of the electronic endoscope 100, and the function as a light source device which supplies illumination light for illuminating the living tissue T near the insertion tube tip portion 111 of the electronic endoscope 100 to the light guide 131 of the electronic endoscope 100.

In this embodiment, the light source unit 400 of the processor 200 for an electronic endoscope includes the light source 430, a collimator lens 440, a spectral filter 410, a filter control unit 420 and a condenser lens 450. The white light emitted from the light source 430 is converted by the collimator lens 440 into a collimated beam, passes through the spectral filter 410, and then is incident on the proximal end portion 131b of the light guide 131 through the condenser lens 450. The spectral filter 410 is a file-r filter of a circular plate type which breaks down the white light from the light source 430 into light of a predetermined wavelength (i.e., selects a wavelength), and selects and outputs light of a narrow band of 400 nm, 405 nm, 410 nm, . . . , 800 nm (a bandwidth of approximately 5 nm) depending on a rotation angle thereof. The rotation angle of the spectral filter 410 is controlled by the filter control unit 420 connected to the controller 530. Since the controller 530 controls the rotation angle of the spectral filter 410 via the filter control unit 420, the light of a predetermined wavelength is incident on the proximal end portion 131b of the light guide 131, and the living tissue T near the insertion tube tip portion 111 is illuminated. Then, light reflected from the living tissue T is converged onto the light-receiving surface of the image pick-up device 141 as described above, and the image signal is transmitted to the image processing unit 500 via the cable 142.

The image processing unit 500 is configured as a device which obtains a plurality of spectral images at intervals of a wavelength of 5 nm from images of the living tissue T obtained via the cable 142. Specifically, when the spectral filter 410 selects and outputs the narrow band light (a bandwidth of approximately 5 nm) of the center wavelengths of 400 nm, 405 nm, 410 nm, . . . , 800 nm, spectral images of the respective wavelengths are obtained.

The image processing unit 500 has the function of processing the plurality of spectral images generated by the spectral filter 410, and generating a color image or an indicator image indicating the position of a diseased portion, as described later. Then, the image processing unit 500 controls the image display device 300 to display the processed spectral image.

It should be noted that, as the spectral filter 410, a Fabry-Perot filter or a filter using a transmission type diffraction grating can be used, for example.

As described above, the image processing unit 500 according to the embodiment has the function of generating the indicator image indicating the position of an area having a high possibility of a diseased portion by using the plurality of spectral images having different wavelengths. In the following, an indicator graph generating function is explained.

Figure 2:
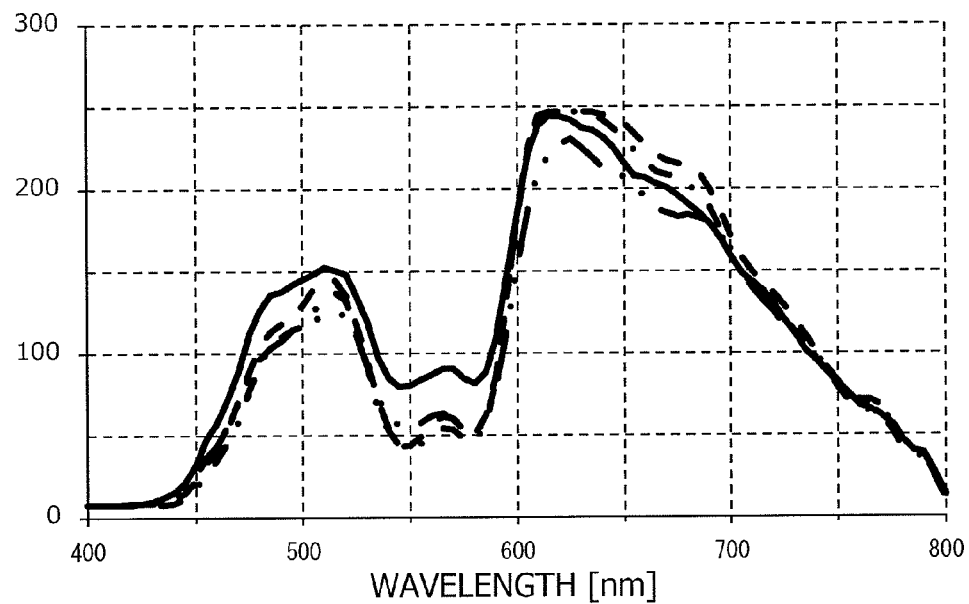
FIG. 2 is a graph illustrating a spectrum of a plurality of image pixels in an image of a gastric mucosa.
Figure 2:
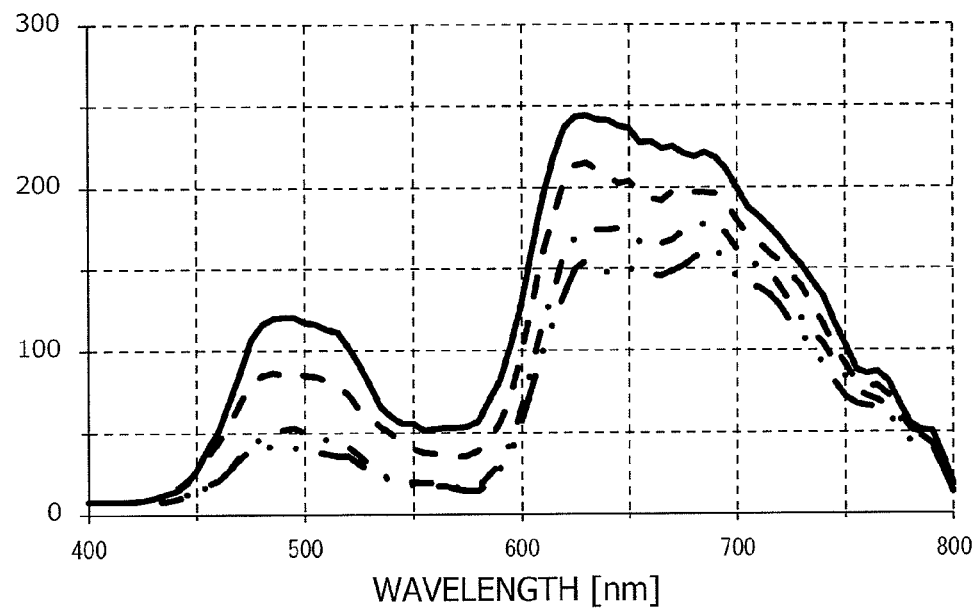

First, an indicator on which an indicator graph generated by the image processing unit 500 according to the embodiment is based is explained. FIG. 2 is a graph representing spectrums of a plurality of image pixels in an image of a gastric mucosa. Specifically, FIG. 2(*a*) represents spectrums of image pixels corresponding to a healthy portion of the gastric mucosa, and FIG. 2(*b*) represents spectrums of image pixels corresponding to a diseased portion of the gastric mucosa. As shown in FIG. 2, the spectrum of the gastric mucosa image has a large peak (a first peak) at the wavelength of 600 nm to 700 nm and a small peak (a second peak) having the center wavelength of 500 nm, regardless of whether the spectrum is a healthy portion or a diseased portion.

As shown in FIG. 2, it is confirmed that the spectrum of an image pixel of the healthy portion is substantially similar to the spectrum of an image pixel of the diseased portion. However, when sensing is performed for a plurality of points distributing two dimensionally, the light amount useful for the sensing varies depending on the point due to difference in an angle between the illumination light and a subject or the difference in distance from the insertion tube tip portion 111 (FIG. 1) of the electronic endoscope 100 to the point. In order to correct the effect of the light amount difference, each spectrum shown in FIG. 2 is subjected to normalization for comparison by replacing the intensity value of each spectrum with information of a relative intensity at each wavelength, regardless of the intensity value of each spectrum shown in FIG. 2. The normalization is performed in the following procedure. In the normalization explained below, with reference to an image pixel whose maximum intensity is largest of all of a plurality of sample image pixels, coefficients for normalizing the other image pixels are obtained.

Let us define a spectrum of each image pixel in the image of the gastric mucosa as $O_n(\lambda_i)$, where n represents a sample number. That is, the spectrum represents the spectral intensity at each two dimensional point. It should be noted that, in the image pixels, image pixels of the healthy portion and image pixels of the diseased portion are mixed. $\lambda_i$ represents each center wavelength of the spectrum, and takes one of values of $\lambda_1=400$ nm, $\lambda_2=405$ nm, ... $\lambda_{81}=800$ nm. First, sample N whose maximum value of $O_n(\lambda)$ is largest of all of the samples is searched for. Then, for $O_n(\lambda)$ of n≠N, a constant Kn satisfying the following expression (1) is obtained.

$$\sum_{i=1}^{81} \log O_N(\lambda_i) = Kn \times \sum_{i=1}^{81} \log O_n(\lambda_i) \quad \text{(EXPRESSION 1)}$$

In the expression, K represents a group of coefficients optimized by calculating the difference in light amount. In this calculation, logarithm representation is used to reflect a chemical density of a substance; however, the normal reflective intensity may also be applied to the calculation.

Figure 3:
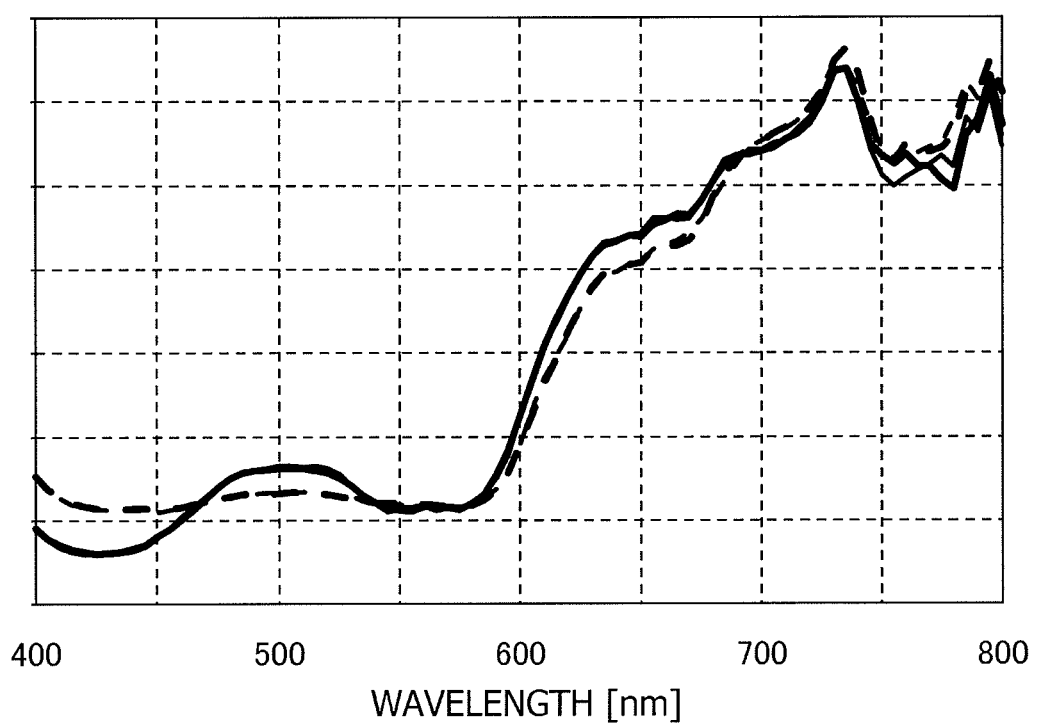
FIG. 3 is a graph illustrating an example of a spectrum obtained after executing a normalization process for the spectrum shown in FIG. 2.

The spectrum obtained by applying the normalization to the spectrum shown in FIG. 2 through the above described procedure is illustrated in FIG. 3. In FIG. 3, a solid line represents the normalized spectrum of the image pixel corresponding to the healthy portion of the gastric mucosa, and a dotted line represents the normalized spectrum of the image pixel corresponding to the diseased portion of the gastric mucosa. As shown in FIG. 3, after the normalization, there is almost no difference between the image pixels for the first peak. On the other hand, it is clear that, regarding the second peak, the image pixel of the healthy portion has higher levels than those of the image pixel of the diseased portion. Furthermore, regarding the level in a valley (around the wavelength of 550 nm) between the first peak and the second peak, the image pixel of the healthy portion is slightly higher than that of the image pixel of the diseased portion. That is, in the wavelength band of 480 to 590 nm, the level of the image pixel of the healthy portion is higher than that of the image pixel of the diseased portion. Therefore, it is understood that the spectral level difference in the band centering at 480 nm to 590 nm can be extracted two dimensionally.

It is known that the wavelength band of 550 to 590 nm is an absorption wavelength band of hemoglobin. In other words, if the level in a portion is low in the wavelength band of 550 to 590 nm is low, there is a high possibility that the portion merely has a high density of blood vessels and information originated from blood is traced. For this reason, in this embodiment, a band having the maximum wavelength smaller than the absorption wavelength band of hemoglobin, e.g., a band around the wavelength of 500 nm (480 to 520), is used as a new marker indicating the diseased portion. That is, separately defined two pieces of information of the wavelength band of 480 to 520 nm and the absorption wavelength band of hemoglobin are used, so that more detailed and more reliable diagnosis support information is provided.

That is, the diagnostic system 1 according to the embodiment uses the levels in the wavelength band centering at 480 to 520 nm as a marker indicating the diseased portion, and an indicator graph indicating a position of an area having a high possibility of a diseased portion is generated. As a result, it is possible to provide diagnosis support information based on the spectral property information containing characteristic variations of various types of diseased portions.

However, it should be noted that the above described normalization process has a heavy processing load, and it is difficult to display an indicator as a real time moving image while performing the normalization process during endoscopic observation. For this reason, in this embodiment, the normalization process is simplified and the indicator is obtained in an extremely short period of time.

As shown in FIG. 2, regarding contribution of the intensity value of each image pixel of the endoscopic image toward the average, components around the first peak is dominant, and contribution of components around the second peak toward the average is low. Therefore, data obtained by calculating a ratio of the intensity value around the second peak with respect to an accumulated value of intensity values of the image pixels in the endoscopic image obtained by the spectral image serves as an indicator indicating the position of an area having a high possibility of a diseased portion as in the case of the intensity value around the wavelength of 500 nm in the above described normalized spectrum (multiplying the intensity value of each image pixel by Kn). In this embodiment, data obtained by dividing the accumulated value of the intensity values of the image pixels by the intensity value around the second peak is used as an indicator indicating the position of an area having a high possibility of a diseased portion. That is, based on the spectral image, the indicator $O_o(x, y)$ at the coordinate $(x, y)$ is obtained from the intensity value $O_I(x, y, \lambda)$ of the image pixel at the coordinate $(x, y)$ by executing calculation according to the following expression (2).

$$O_O(x, y) = \frac{\sum_{i=1}^{81} O_I(x, y, \lambda_i)}{\sum_{i=ma}^{mb} O_I(x, y, \lambda_i)} \times M \quad \text{(EXPRESSION 2)}$$

As in the case of the expression (1), in the above described expression (2), $\lambda_i$ is each center wavelength in the spectrum, and takes one of values of $\lambda_1=400$ nm, $\lambda_2=405$ nm, ... $\lambda_{81}=800$ nm. "ma" and "mb" are natural numbers satisfying ma≤mb, and are appropriately selected so that the wavelength band $\lambda_{ma}$ to $\lambda_{mb}$ is included in a wavelength band around the second peak. M is a coefficient which is appropriately defined so that $O_o(x, y)$ falls within a proper range (e.g., a range of 0 to 1) (i.e., so that the maximum value of $O_o(x, y)$ becomes a proper value). As described above, since $O_o(x, y)$ obtained from the expression (2) is a value defined by dividing the accumulated value of the intensities of the image pixels of the endoscopic image by the intensity value around the second peak, the coordinate $(x, y)$ having a large $O_o(x, y)$ obtained by the expression (2) is assumed to be an area having a high possibility of a diseased portion.

Figure 4:
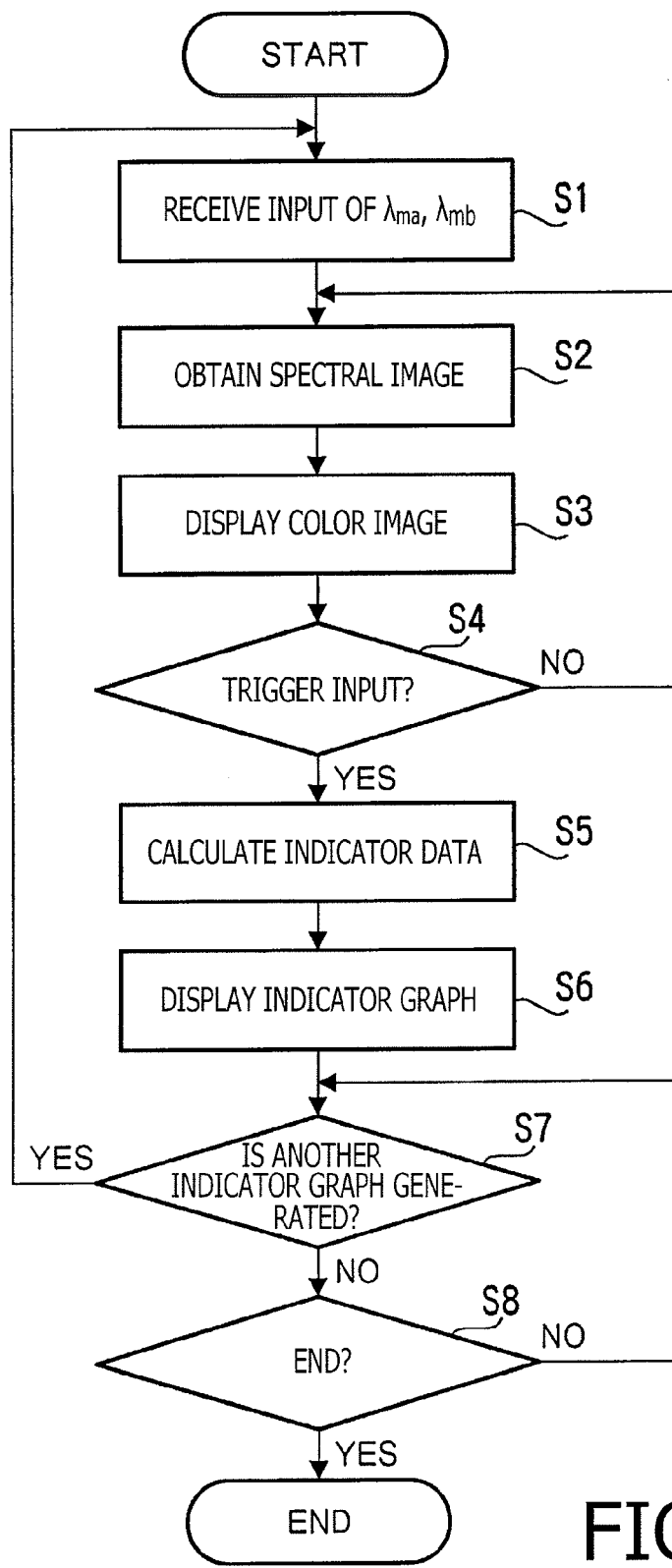
FIG. 4 is a flowchart illustrating a routine for executing representation of an indicator graph, executed by a spectral image processing unit of the diagnostic system according to the embodiment of the invention.

In the following, a procedure for generating an indicator graph by the diagnostic system 1 according to the embodiment is explained. FIG. 4 is a flowchart illustrating a routine for generating the indicator graph and displaying the indicator graph on the image display device 300 executed by the image processing unit 500 according to the embodiment. The routine is executed at a time of power-on of the image processing unit 500.

When the routine is started, step S1 is executed. In step S1, the image processing unit 500 displays, the image display device 300, a message requesting input of the lower limit $\lambda_{ma}$ and the upper limit $\lambda_{mb}$ of the wavelength band to be compared with the accumulated value (a numerator of the right side of the expression (2)) of the intensity values for generating the indicator graph, and accepts input of $\lambda_{ma}$ and $\lambda_{mb}$. When $\lambda_{ma}$ and $\lambda_{mb}$ are inputted through an input unit (not shown) (e.g., a keyboard) of the image processing unit 500, the process proceeds to step S2.

In step S2, the image processing unit 500 transmits a control signal for controlling the filter control unit 420 to obtain the spectral image. When receiving the control signal, the filter control unit 420 controls the rotation angle of the spectral filter 410 so as to sequentially select the narrow band (a bandwidth of approximately 5 nm) of light of 400, 405, 410, ... 800 nm. The image processing unit 500 shoots the spectral image obtained at each wavelength and stores the spectral image in the temporary memory 520. Then, the process proceeds to step S3.

In step S3, three images having the center wavelengths of 435 nm, 545 nm and 700 nm are extracted from the spectral images obtained at step S2, and one piece of color image data in which an image of the center wavelength of 435 nm is stored in a blue plane, an image of the center wavelength of 545 nm is stored in a green plane and an image of the center wavelength of 700 nm is stored in a red plane is generated. As described above, the color image data is obtained from a spectral image of a blue color wavelength of 435 nm, a spectral image of a green color wavelength of 545 nm and a spectral image of a red color wavelength of 700 nm, and is a color image equivalent to the endoscopic image for normal observation. Then, the image processing unit 500 transmits the generated color image data to the video memory 540, and displays the color image on the left side in the screen of the image display device 300.

In step S4, it is checked whether a trigger input designating generation of the indicator graph occurs through use of the input unit of the image processing unit 500 during execution of steps S2 and S3. When the trigger input does not occur (S4: NO), the process proceeds to step S2 to obtain again the spectral image. That is, unless the trigger input occurs, the color image obtained from the spectral image is sequentially updated and continuously displayed on the image display unit 300. On the other hand, when the trigger input occurs during execution of steps S2 and S3 (S4: YES), the process proceeds to step S5.

In step S5, from $\lambda_{ma}$ and $\lambda_{mb}$ inputted at step S1 and the spectral image obtained at step S2, the indicator is generated using the expression (2). Then, the process proceeds to step S6.

In step S6, the indicator graph graphically showing the indicator generated in step S5 is displayed on the right side in the screen of the image display device 300. As a result, on the screen of the image display device 300, the color image of the endoscopic image and the indicator graph are arranged side by side. Therefore, a user of the diagnostic system 1 is able to judge which area in the color image is a diseased portion, by making a comparison between the color image and the indicator graph. Then, the process proceeds to step S7.

In step S7, the image processing unit 500 displays a message inquiring whether to generate the indicator graph again on the image display device 300, and receives input through the input unit. When the user of the diagnostic system 1 selects generating again the indicator graph by operating the input unit (S7: YES), the process returns to step S1. On the other hand, when an input for generating again the indicator graph is not made for a predetermined period of time (e.g., for several seconds) (S7: NO), the process proceeds to step S8.

In step S8, the image processing unit 500 displays a message inquiring whether to terminate displaying of the indicator graph on the image display device 300, and receives input through the input unit. When the user of the diagnostic system 1 selects terminating displaying of the indicator graph by operating the input unit (S8: YES), the routine is terminated. On the other hand, when an input for displaying the indicator graph is not made for a predetermined period of time (e.g., for several seconds) (S8: NO), the process proceeds to step S7.

As described above, by executing the routine shown by the flowchart in FIG. 4 through the image processing unit 500, the indicator graph which is referred to for estimating the position of the diseased portion is displayed on the image display device 300 together with the color image of the endoscopic image.

As described above, in this embodiment, the user of the diagnostic system 1 manually inputs the wavelength band $(\lambda_{ma}, \lambda_{mb})$ serving as a marker for the diseased portion. However, the present invention is not limited to the above described configuration. The wavelength band serving as a marker for the diseased portion may be provided as a fixed value (e.g., 480 nm to 520 nm, or 500 nm).

In this embodiment, the accumulated value of the intensity values of the image pixels and the intensity value around the second peak are obtained from the spectral images of different wavelengths, and are used as an indicator indicating the position having a high possibility of a diseased portion. However, the present invention is not limited to such a configuration. The numerator of the expression (2) (i.e., the accumulated value of the intensity values of the image pixels) does not require data of a spectral image of a particular wavelength, and the calculation can be made by using a certain type of intensity information of a monochrome image. Therefore, in place of the process for obtaining the accumulated value of the intensity values of the image pixels, the intensity values of the image pixels by white light may be obtained after retracting the spectral filter 140. If the image pick-up device 141 has a color filter on the front side thereof, a color filter of Bayer-array of R(red)-GY(gray)-G(green)-B(blue) may be arranged in place of a typical Baye-array of R(red)-G(green)-G(green)-B(blue), and intensity information obtained by a filter of GY(gray) may be used after retracing the spectral filter 140. With this configuration, it becomes possible to execute the calculation process of the expression (2) simply and at a high speed because there is no necessity to obtain the accumulated value of the intensity values of the image pixels of the spectral images of different wavelengths.

EXAMPLE

Figure 5:
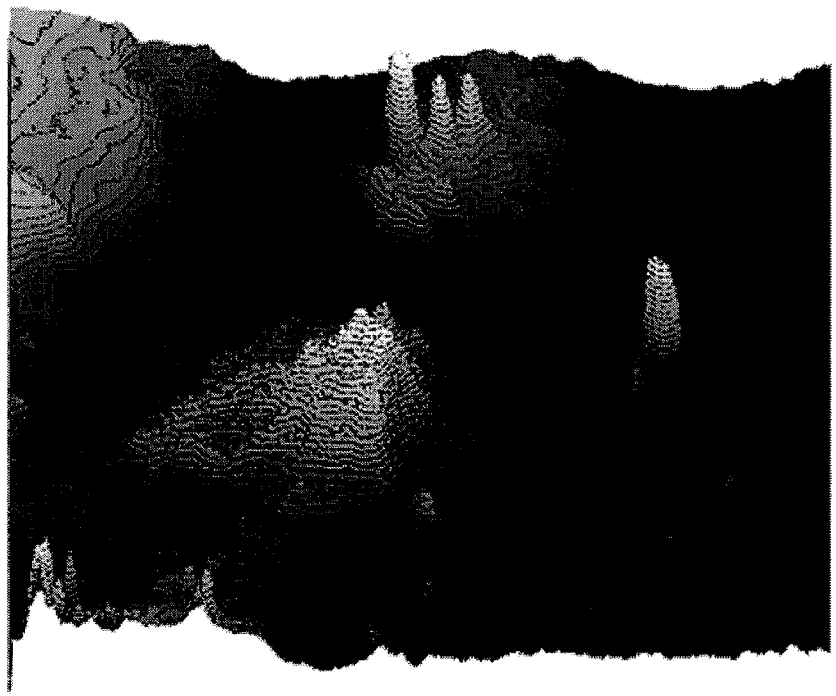
FIG. 5 shows an indicator graph according to an example.

Hereafter, an example of a diagnosis of a gastric mucosa using the diagnostic system 1 according to the embodiment is shown. FIG. 5 is an indicator graph defined by mapping the indicator $O_o(x, y)$ obtained by processing the spectral image of the endoscopic image through the diagnostic system 1 according to the embodiment. It should be noted that, for obtaining the indicator $O_o(x, y)$, $\lambda_{ma}$ and $\lambda_{mb}$ of the above described expression (2) is set for 500 nm.

As shown in FIG. 5, in this example, the indicator graph is represented as a contour graph, and an area having a high indicator $O_o(x, y)$ (i.e., an area having a high possibility of a diseased portion) is represented in a low density (i.e., more white) and to be a higher position in the contour graph. Therefore, it is possible to estimate the position of the diseased portion from the indicator graph.

In this example, the indicator graph is represented as a contour graph; however, the present invention is not limited to the above described configuration. For example, the position of the diseased portion may be represented simply by gradation (i.e., an indicator graph where the intensity of each coordinate (x, y) is proportional to $O_o(x, y)$), or a mark, such as a frame, may be superimposed, in an area where $O_o(x, y)$ exceeds a predetermined threshold, on the color image displayed on the image display device 300, without using an indicator graph.

What is claimed is:

1. A diagnostic system, comprising:
a spectral image imaging device that captures a predetermined number of spectral images in a body cavity at each of a plurality of predetermined narrow band wavelengths of light, the predetermined number of spectral images being spaced apart at predetermined intervals of wavelengths within a predetermined wavelength range, by switching the plurality of predetermined narrow band wavelengths of light sequentially;
an image processor that obtains the predetermined number of spectral images, extracts, from the predetermined number of spectral images, images having a green color center wavelength, a blue color center wavelength and a red color center wavelength, and calculates an indicator, to indicate an area having a high possibility of a diseased portion from the spectral images;
a monitor on which an indicator image based on the indicator is displayed; and
an input device that receives an input from a user,
wherein the image processor calculates, as the indicator, a ratio between an accumulated value of intensity values of all of the predetermined number of spectral images in the predetermined wavelength range and an accumulated value of intensity values of spectral images in a particular wavelength band in the predetermined wavelength range, for each coordinate in the predetermined number of spectral images, and
wherein, based on the input from the user, the input device sets the particular wavelength band within a range of 480 nm to 520 nm.

2. The diagnostic system according to claim 1, wherein the image processor operates to display, on the monitor, an indicator graph which is a graphic representation of the indicator.

3. The diagnostic system according to claim 2, wherein:
the image processor generates color image data by combining data of wavelength bands of a blue color, a green color and a red color of the spectral images; and
the color image data and the indicator graph are arranged side by side and are displayed on the monitor.

4. The diagnostic system according to claim 1, wherein the predetermined wavelength range is 400 nm to 800 nm.

5. The diagnostic system according to claim 1, wherein the spectral image imaging device changes the predetermined narrow band wavelengths of light at the predetermined intervals of 5 nm.

6. The diagnostic system according to claim 1, wherein the spectral image imaging device comprises:
a light source that emits white light;
a spectral filter that selects and outputs one of the plurality of predetermined narrowband wavelengths of light at one time;
a filter controller that controls the spectral filter to sequentially output the plurality of predetermined narrowband wavelengths of light from the spectral filter; and
an image pick-up device that receives light output from the spectral filter and reflected by the body cavity.

7. The diagnostic system according to claim 1, wherein the predetermined intervals of wavelengths within the predetermined wavelength range are uniformly spaced.

8. The diagnostic system according to claim 1, wherein the predetermined intervals of wavelengths are determined independently of a color of the light of the spectral images.

* * * * *